United States Patent [19]

Campbell et al.

[11] Patent Number: 4,569,945

[45] Date of Patent: Feb. 11, 1986

[54] DIARYLINDANE-1,3-DIONES, THEIR PREPARATION AND USE

[75] Inventors: Alexander C. Campbell, Larbert; Donald F. M. Stevenson, Edinburgh, both of Scotland

[73] Assignee: Akzo N.V., Arnhem, Netherlands

[21] Appl. No.: 660,287

[22] Filed: Oct. 12, 1984

[30] Foreign Application Priority Data

Oct. 14, 1983 [GB] United Kingdom ............... 8327598

[51] Int. Cl.[4] .................. A61K 31/12; C07C 49/747
[52] U.S. Cl. ................................ 514/681; 568/327; 568/319; 568/306; 564/428; 514/677; 514/569
[58] Field of Search .............. 568/327, 319, 306; 564/428; 260/465 D; 424/331, 325; 514/681, 677, 564

[56] References Cited

U.S. PATENT DOCUMENTS

| | | | |
|---|---|---|---|
| 3,413,353 | 11/1968 | Nauta et al. | 568/327 |
| 3,784,605 | 1/1974 | Durden et al. | 568/327 |
| 3,784,606 | 1/1974 | Holland et al. | 568/327 |
| 3,803,240 | 4/1974 | Durden et al. | 568/327 |
| 3,879,468 | 4/1975 | Durden et al. | 568/327 |
| 3,976,681 | 8/1976 | Cragoe et al. | 568/327 |
| 3,978,231 | 8/1976 | Buckle et al. | 424/331 |

FOREIGN PATENT DOCUMENTS 867138  7/1962  France ................... 568/327

*Primary Examiner*—James H. Reamer
*Attorney, Agent, or Firm*—Wegner & Bretschneider

[57] ABSTRACT

The invention is dealing with arylindane-1,3-diones of the formula:

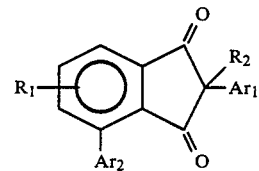

which can be used in the treatment of inflammatories, psoriasis and asthma.

9 Claims, No Drawings

DIARYLINDANE-1,3-DIONES, THEIR PREPARATION AND USE

The invention is dealing with arylindane-1,3-dione compounds, a method for the preparation thereof and pharmaceutical formulations concerning these compounds.

Arylindane-1,3-diones have already been reported to possess pharmacological activity. Since most indanediones which exhibit interesting anti-inflammatory activity have also been shown to possess anti-coagulant activity, they are rendered unacceptable for the development of drugs for treating inflammatory diseases such as rheumatoid arthritis.

The present invention concerns novel arylindane-1,3-diones showing pronounced anti-inflammatory activity, but little anti-coagulant effect. This profile renders the compounds more suitable to be used as anti-inflammatory compounds. The compounds can furthermore be used in the treatment of psoriasis and asthma.

The compounds according to the invention are diarylindane-1,3-diones of the general formula I:

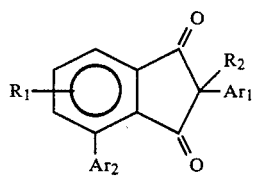

I or pharmacologically acceptable salts thereof, wherein: $Ar_1$ and $Ar_2$ represent both an aromatic group that may be substituted with one or more of the following substituents alkyl, alkoxy or amino-alkyl with 1-6 carbon atoms, cyclo-alkyl or cyclo-alkyl-alkyl with 4-8 carbon atoms, phenyl, halogen, nitro, amino, hydroxy, or trifluoromethyl, $R_1$ represents hydrogen, halogen or alkyl or alkoxy with 1-6 carbon atoms, and $R_2$ represents hydrogen, halogen or hydroxy.

Advantageously, $Ar_1$ and $Ar_2$ are substituted or unsubstituted phenyl or naphthyl groups.

Particularly preferred compounds according to the invention are compounds wherein $Ar_1$ represents a mono- or polyhalogen substituted phenyl group.

The group $Ar_2$ is preferably an unsubstituted phenyl, or a halogen or alkoxy substituted phenyl group.

A preferred embodiment of the invention comprises the compound 2-(p-chlorophenyl)-4-phenylindane-1,3-dione.

Pharmaceutically acceptable salts of the compounds according to the invention are preferably alkali or earth alkali metal salts, particularly sodium or potassium salts.

The compounds according to the invention (with $R_2$ is H) can be prepared by rearrangement of the corresponding 1-, or 3-arylidene compounds of the general formulae II and III respectively

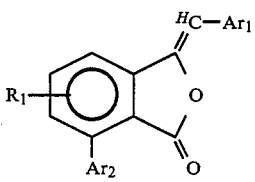

II

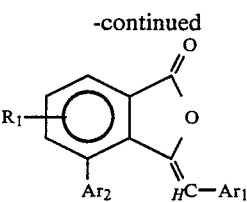

III

To prepare a compound I in which $R_2$ is halogen, the compound thus obtained (I, $R_2$=H) is subsequently halogenated in the usual manner and a compound I in which $R_2$ is hydroxy can be prepared by hydrolysis of the halogen compound (I, $R_2$=halogen, especially bromo) e.g. with silvernitrate, ethanol and water.

This rearrangement can preferably be established by reacting the arylidene compounds II or III with a strong base, such as sodium methoxide.

The starting arylidene compounds II and III can be prepared by methods known per se for the preparation of analogous compounds. Advantageously as a starting material can be used the corresponding substituted phtalic anhydride of the general formula IV or the lactones of the formulae VA or VB:

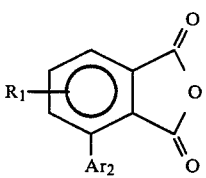

IV

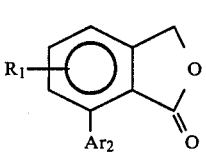

VA

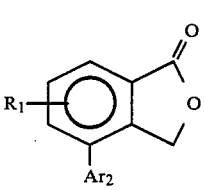

VB

The arylidene compounds II and III can be formed for example by reacting the compound IV with a compound of the general formula VI or a salt thereof

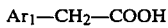

$Ar_1$—$CH_2$—COOH   VI or reacting compound VA or VB with the aldehyde VII:

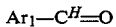

$Ar_1$—$C^H$=O   VII by methods known per se.

The arylidene compounds II or III or a mixture thereof may be isolated prior to rearrangement, or the compound according to the invention may be formed in the same reaction medium in which the arylidene compound(s) were formed without isolating the latter.

By alkyl in the definitions of $Ar_1$, $Ar_2$ and R is meant a linear or branched alkyl group with 1 to 6 carbon atoms and more preferably with 1-4 carbon atoms such as methyl, ethyl n-propyl, isopropyl, n-butyl, tert.-butyl, sec.-butyl.

By cyclo alkyl is meant a group with a saturated cyclic carbon atom structure with 5–8 carbon atoms, viz. cyclopentane, cyclohexane, cycloheptane and cyclo-octane. By cyclo-alkyl-alkyl is meant a group comprising a cyclo-alkyl group substituted at an alkyl group, with all together 4–8 carbon atoms, such as cyclopropylmethyl, cyclobutylmethyl and cyclopentylmethyl.

The alkyl part of the alkoxy group and amino alkyl group has the same meaning as the alkyl group defined above.

By halogen is meant fluorine, chlorine, bromine, iodine, whereby chlorine is to be preferred.

The invention also concerns pharmaceutical preparations containing one or more compounds according to the invention. The compounds according to the invention can be administered enterally or parenterally. For enteral administration the compounds according to the invention (if desired, mixed with suitable carriers) can be formed to pharmaceutical preparations such as pills, suppositories, capsules, powders and tablets. For parenteral administration the compounds according to the invention can be compounded into an injectable preparation by dissolving, emulgating or dispersing them in a suitable liquid medium. Compounds according to the invention also can be incorporated in for example sprays, ointments, cremes or gels for local application to the skin or to mucous surfaces.

The compounds according to the invention are preferably administered in a daily dosage of from 1 µg to 25 mg per kg bodyweight depending upon the way of administration. For parenteral administration to human beings the preferred daily dosage varies from 0,1 to 25 mg and for enteral administration from 1 to 400 mg.

In sprays, cremes, gels or ointments the preferred dosage varies from 0,01 to 25% of the total composition.

The compounds of the invention may also occur in their enol form.

EXAMPLE I 2,4-Diphenylindane-1,3-dione

A. Trans-1-phenyl-1,3-butadiene

The preparation of this diene from cinnamaldehyde was carried out according to the method described by Grummit and Becker (Organic Synthesis, Vol. 30, pp. 75–77). The yield was approximately 60%, boiling point 69°–72° C. at 0.04 kPa.

B. 3-Phenyl-cis-1,2,3,6-tetrahydrophthalic anhydride

This anhydride was prepared from the product obtained under A and maleic anhydride essentially by the method described by Diels, Alder and Pries (Berichte, 1929, 62, 2081). The resulting product had a melting point of 119°–121° C.

C. 3-Phenylphthalic anhydride 7.8 g of N-bromosuccinimide was added in portions to a solution of 5 g of the product obtained under B in 75 ml of 1,2-dichloroethane containing a catalytic amount of benzoyl peroxide. The mixture was heated under reflux for 1.5 hour and then cooled. The precipitated succinimide was filtered off and the reaction mixture poured out into 200 ml of water. The organic phase was washed with water and dried over magnesiumsulphate. Removal of the solvent under reduced pressure afforded a mixture of 7.8 g of bromo compounds which was dissolved in 120 ml of dry acetone, 5.5 g of anhydrous sodium iodide added and the mixture heated under reflux for 2 hours. The precipitated solid was filtered off and the solvent removed under reduced pressure. The residue was dissolved in methylene chloride and the solution washed with 50 ml of 10% solution of sodiumsulphite, and then with water. After drying over magnesiumsulphite, the solvent was removed under reduced pressure and the residue recrystallized from acetonitrile to afford 3.2 g of 3-phenylphthalic anhydride as prisms, melting point 148°–149° C.

D. 2,4-diphenylindane-1,3-dione 23.7 g of 3-phenylphthalic anhydride, 14.4 g of phenylacetic acid and 475 mg of anhydrous sodium acetate were heated under a nitrogen atmosphere at 230°–250° C. until evolution of carbon dioxide ceased (approximately 3 hours). The reaction mixture was cooled, dissolved in methylene chloride and the solution was washed with 10% sodiumbicarbonate solution and then with water. After drying over magnesium sulphate and evaporation of the solvent the crude phenylidene compound was obtained as a residual solid.

This solid material was added to a solution of 8.7 g of sodiummethoxide in 250 ml of methanol, and the mixture was heated under reflux for 4 hours. The methanol was removed under reduced pressure, 250 ml of water were added and the mixture was filtered through dicalite. The filtrate was acidified and the precipitated solid was filtered, dried and recrystallized twice from chloroform-ethanol to give 10.9 g of 2,4-diphenylindan-1,3-dione, melting point 166°–168° C.

EXAMPLE II

By methods analogous to Example I the following compounds were prepared:

A. 2-(4-chlorophenyl)-4-phenylindane-1,3-dione, melting point (m.p. 160°–162° C.)

B. 2-(4-methoxyphenyl)-4-phenylindane-1,3-dione, m.p. 173°–175° C.

C. 2-(3,4-dichlorophenyl)-4-phenylindane-1,3-dione, m.p. 142°–144° C.

D. 2-(4-n-propoxyphenyl)-4-phenylindane-1,3-dione, m.p. 233°–235° C.

E. 2-(4-biphenyl)-4-phenylindane-1,3-dione, m.p. 233°–235° C.

F. 2-(4-amino-n-propylphenyl)-4-phenylindane-1,3-dione, m.p.

G. 2-(4-trifluoromethylphenyl)-4-phenylindane-1,3-dione, m.p. 159°–160° C.

H. 2-(3,5-dichlorophenyl)-4-phenylindane-1,3-dione, m.p.

I. 2-(2,4-dichlorophenyl)-4-phenylindane-1,3-dione, m.p. 161°–164° C.

J. 2-(4-nitrophenyl)-4-phenylindane-1,3-dione, m.p. 170°–172° C.

K. 2-(4-cyclohexylphenyl)-4-phenylindane-1,3-dione, m.p. 190°–192° C.

L. 2,4-di-(4-chlorophenyl)-indane-1,3-dione, m.p. 152°–154° C.

M. 2-(4-chlorophenyl)-4-(4-methoxyphenyl)-indane-1,3-dione, m.p. 101°–104° C.

N. 2-(4-chloro-3-iodophenyl)-4-phenylindane-1,3-dione, m.p. 160°–162° C.

O. 2-(4-chlorophenyl)-4-phenyl-6-bromo-indane-1,3-dione, m.p. 160°–163° C.

P. 2-(4-chlorophenyl)-4-phenyl-5-bromo-indane-1,3-dione

Q. 2-(4-chlorophenyl)-4-phenyl-7-bromo-indane-1,3-dione, m.p. 200°-204° C.

EXAMPLE III

2-Bromo-2-(p-chlorophenyl)-4-phenylindane-1,3-dione

N-bromosuccinimide (0.3 g ) was added portionwise over 15 minutes to a stirred solution of 2-(p-chlorophenyl)-4-phenylindane-1,3-dione (0.5 g) containing benzoyl peroxide (0.01 g) at ambient temperature and the reaction was allowed to stir for a further 15 minutes. The solvent was removed under reduced pressure and the crude product was chromatographed on silica. The fraction eluted with toluene was recrystallised from diethyl etherhexane to give 2-bromo-2-(p-chlorophenyl)-4-phenylindane-1,3-dione, m.p. 121-123.

EXAMPLE IV 2-(p-chlorophenyl)-2-hydroxy-4-phenylindane-1,3-dione

A mixture of 2-bromo-2-(p-chlorophenyl)-4-phenylindane-1,3-dione (0.3 g), silver nitrate (0.15 g) ethanol (3 ml) and water (3 ml) was heated under reflux for 2 hours. After cooling, the precipitated solid was filtered off. The solvent was removed from the filtrate under reduced pressure and the residual solid was chromatographed in silica. Recrystallisation from ethanol-water of the fraction eluted with ethyl acetate afforded 2-(p-chlorophenyl)-2-hydroxy-4-phenylindane-1,3-dione, m.p. 161-163.

We claim:

1. A compound of the formula:

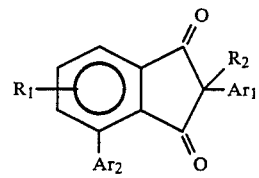

or a pharmaceutically acceptable salt thereof, wherein $Ar_1$ and $Ar_2$ represent both a phenyl or naphthyl group that may be substituted with one or more of the following substituents: alkyl, alkoxy or amino-alkyl with 1-6 carbon atoms, cyclo-alkyl or cyclo alkyl-alkyl with 4-8 carbon atoms, phenyl, halogen, nitro, amino, hydroxy or trifluoromethyl, $R_1$ represents hydrogen, halogen or alkyl or alkoxy with 1-6 carbon atoms, and $R_2$ represents hydrogen, halogen or hydroxy.

2. A compound according to claim 1, characterized in that $Ar_1$ represents a mono- or polyhalogen substituted phenyl group.

3. A compound according to claim 1, characterized in that $Ar_2$ represents a phenyl or a halogen or alkoxy substituted phenyl group.

4. The compound 2-(p-chlorophenyl)-4-phenylindane-1,3-dione, according to claim 1.

5. The compound 2-(p-chlorophenyl)-2-bromo-4-phenylindane-1,3-dione according to claim 1.

6. A compound according to claim 2, characterized in that $Ar_1$ represents a mono- or polyhalogen substituted phenyl group.

7. A compound according to claim 2, characterized in that $Ar_2$ represents a phenyl or a halogen or alkoxy substituted phenyl group.

8. A compound according to claim 2, characterized in that $Ar_2$ represents a phenyl or a halogen or alkoxy substituted phenyl group.

9. A pharmaceutical composition for anti-inflammatory use comprising an anti-inflammatory effective amount of a compound of claim 1 and a pharmaceutically acceptable carrier therefor.

* * * * *